United States Patent [19]
Mahdavieh et al.

[11] Patent Number: 5,345,514
[45] Date of Patent: Sep. 6, 1994

[54] METHOD FOR INSPECTING COMPONENTS HAVING COMPLEX GEOMETRIC SHAPES

[75] Inventors: Yaghoub Mahdavieh, West Chester, Ohio; Kristina H. V. Hedengren, Schenectady, N.Y.

[73] Assignee: General Electric Company, Cincinnati, Ohio

[21] Appl. No.: 772,761

[22] Filed: Sep. 16, 1991

[51] Int. Cl.$^5$ .................... G06K 9/00; G01R 33/00
[52] U.S. Cl. .......................... 382/8; 382/25; 324/240
[58] Field of Search .............. 382/1, 8, 25; 364/481; 358/106; 356/32; 324/209, 233, 238, 240

[56] References Cited

U.S. PATENT DOCUMENTS

| | | | |
|---|---|---|---|
| 4,591,784 | 5/1986 | Kolitsch et al. | 324/208 |
| 4,628,261 | 12/1986 | Hüschelrath et al. | 324/240 |
| 4,821,204 | 4/1989 | Hüschelrath | 364/481 |
| 5,028,100 | 7/1991 | Valleau et al. | 324/233 |
| 5,182,775 | 1/1993 | Matsui et al. | 382/8 |

FOREIGN PATENT DOCUMENTS

| | | |
|---|---|---|
| 0185187 | 11/1985 | European Pat. Off. . |
| 111056A | 6/1984 | Japan . |
| 1427284 | 9/1988 | U.S.S.R. . |
| 2010492A | 6/1979 | United Kingdom . |
| 2192993A | 1/1988 | United Kingdom . |

OTHER PUBLICATIONS

I.E.E.E. Transactions on Magnetics, MAG-23 (1987) Sep., No. 5 (Part II of Two Parts) New York, N.Y., "Data Acquisition for Experimental Verification of an Eddy Current Model for Three Dimensional Inversion", by J. A. Nyenhuis et al.
I.E.E.E. Transactions on Magnetics, 27 (1991) Nov., No. 6, New York, "Eddy Current Testing of Anomalies in Conductive Materials, Part I: Qualitative Imaging via Diffraction Tomography Techniques", Riadh Zorgati et al.
I.E.E.E. Transactions on Magnetics, MAG-22 (1986) Nov., No. 6, New York, N.Y., "Verification of an Eddy-Current Flaw Inversion Algorithm", by Harold A. Sabbagh et al.
I.E.E.E.-I.E.C.EJ.-A.S.J. International Conference on Acoustics, Speech and Signal Processing, Apr. 7–11, 1986, "Automatic Classification and Recognition of Defects in an Eddy Current Non Destructive Testing", by P. Simard et al.
R. O. McCary, Review of Progress in Quantitative Nondestructive Evaluation, vol. 9, 1990, pp. 773–780.

*Primary Examiner*—Leo H. Boudreau
*Assistant Examiner*—Chris Kelley
*Attorney, Agent, or Firm*—Jerome C. Squillaro; Bernard E. Shay

[57] ABSTRACT

A method for inspecting a component of a gas turbine engine or the like having a plurality of similarly shaped structural portions, such as the gear teeth of a gear, the dovetail slots of a turbine disk or the like, includes the steps of: scanning a surface of at least one of the similarly shaped structural portions with an eddy current probe to induce eddy currents in the component; generating a two-dimensional image of the at least one portion from eddy current signals received during scanning, the image including a multiplicity of pixels arranged in a two-dimensional array and each pixel having a gray scale intensity responsive to the eddy current induced in the component at a component location corresponding to a position of the pixel in the matrix array; preprocessing the image to substantially reduce any signals or changes in the gray scale intensity of any pixels relative to the background pixel intensities of the image caused by geometrical characteristics and background noise common to all similarly shaped structuaral portions; identifying any suspected defect regions from the preprocessed image; determining a defect signal for each suspected defect region; and rejecting the component if any defect signal exceeds a predetermined reference value.

34 Claims, 6 Drawing Sheets

|       | $I_{11}$ | $I_{12}$ | $I_{13}$ | $I_{14}$ | $I_{15}$ | $I_{16}$ | $I_{17}$ | $I_{18}$ | $I_{19}$ | $I_{1j}$ |
|-------|----------|----------|----------|----------|----------|----------|----------|----------|----------|----------|
|       | $I_{21}$ | $I_{22}$ | $I_{23}$ | $I_{24}$ | $I_{25}$ | $I_{26}$ | $I_{27}$ | $I_{28}$ | $I_{29}$ | $I_{2j}$ |
|       | $I_{31}$ | $I_{32}$ | $I_{33}$ | $I_{34}$ | $I_{35}$ | $I_{36}$ | $I_{37}$ | $I_{38}$ | $I_{39}$ | $I_{3j}$ |
|       | $I_{41}$ | $I_{42}$ | $I_{43}$ | $I_{44}$ | $I_{45}$ | $I_{46}$ | $I_{47}$ | $I_{48}$ | $I_{49}$ | $I_{4j}$ |
|       | $I_{51}$ | $I_{52}$ | $I_{53}$ | $I_{54}$ | $I_{55}$ | $I_{56}$ | $I_{57}$ | $I_{58}$ | $I_{59}$ | $I_{5j}$ |
|       | $I_{61}$ | $I_{62}$ | $I_{63}$ | $I_{64}$ | $I_{65}$ | $I_{66}$ | $I_{67}$ | $I_{68}$ | $I_{69}$ | $I_{6j}$ |
|       | $I_{71}$ | $I_{72}$ | $I_{73}$ | $I_{74}$ | $I_{75}$ | $I_{76}$ | $I_{77}$ | $I_{78}$ | $I_{79}$ | $I_{7j}$ |
|       | $I_{i1}$ | $I_{i2}$ | $I_{i3}$ | $I_{i4}$ | $I_{i5}$ | $I_{i6}$ | $I_{i7}$ | $I_{i8}$ | $I_{i9}$ | $I_{ij}$ |

| j \ i | 1 | 2 | 3 | 4 | 5 | 6 | 7 |
|-------|---|---|---|---|---|---|---|
| 1 | 0 | 0 | 0 | 1 | 0 | 0 | 0 |
| 2 | −1 | 0 | 0 | 0 | 0 | 0 | 1 |
| 3 | 0 | 0 | 0 | −1 | 0 | 0 | 0 |

|   | 1 | 2 | 3 | 4 | 5 | 6 | 7 | 8 | 9 | j |
|---|---|---|---|---|---|---|---|---|---|---|
| 1 | 0 | 0 | 0 | 0 | 0 | 0 | 1 | 0 | 0 | 0 |
| 2 | 0 | 1 | 1 | 0 | 0 | 1 | 1 | 1 | 0 | 0 |
| 3 | 0 | 1 | 0 | 0 | 0 | 0 | 0 | 1 | 0 | 0 |
| 4 | 0 | 0 | 1 | 1 | 1 | 1 | 1 | 1 | 0 | 0 |
| 5 | 0 | 0 | 1 | 1 | 1 | 1 | 1 | 1 | 0 | 0 |
| 6 | 0 | 0 | 1 | 1 | 1 | 1 | 1 | 1 | 0 | 0 |
| 7 | 0 | 0 | 0 | 0 | 0 | 0 | 0 | 0 | 0 | 0 |
| i | 0 | 0 | 0 | 0 | 0 | 0 | 0 | 0 |   | 0 |

FIG. 6

| 1 | 1 | 1 | 1 | 1 | 1 | 1 | 1 | 1 |
|---|---|---|---|---|---|---|---|---|
| 1 | 1 | 1 | 1 | 1 | 1 | 1 | 1 | 1 |

METHOD FOR INSPECTING COMPONENTS HAVING COMPLEX GEOMETRIC SHAPES

BACKGROUND OF THE INVENTION

The present invention relates to the inspection of components and, more particularly, to an improved method for automatically inspecting gas turbine engine components having complex geometric shapes using eddy current techniques.

Eddy current inspection is a commonly used technique for detecting discontinuities or flaws in the surface of a gas turbine engine component. Eddy current techniques are based on the principle of electromagnetic induction in which eddy currents are induced within the material under inspection. Eddy currents are induced in a test specimen by alternating magnetic fields created in the coil of an eddy current probe when the probe is moved into proximity with the component under test. Changes in the flow of eddy currents are caused by the presence of a discontinuity or a crack in the test specimen. The altered eddy currents produce a secondary field which is received by the eddy current probe coil or by a sensor coil in the eddy current probe which converts the altered secondary magnetic field to an electrical signal which may be recorded on a strip chart. An eddy current machine operator may then detect and size flaws by monitoring and reading the signals recorded on the strip chart. Flaws or defects are detected if the electrical signal exceeds a predetermined voltage threshold.

Present eddy current inspection methods work satisfactorily when the components under inspection have simple geometrical shapes, such as holes, flat plates or the like. However, when the component under test has a complex geometrical shape, such as the dovetail slots of a high pressure or low pressure turbine disk, fan disk, high pressure compressor disk, teeth of a gear or the like, the complex geometry of these components such as edges, transitions between convex, concave and flat regions, produces contributions to the eddy current signals which make it difficult to distinguish between defects and non-defects.

A presently used method of detecting cracks or defects in a complex gas turbine engine component involves scanning a portion of the surface of the complex component with an eddy current probe and converting the received eddy current signals to a two-dimensional digital image. The two-dimensional image is then matched or compared to a chosen template by known image analysis techniques, such as convolution, to detect a defect or flaw. The template is chosen according to the active region of the eddy current probe as well as the size and shape of the defects desired to be detected. The image analysis matching technique will detect a defect only if the size and shape of the defect correspond substantially to that represented by the chosen template. Different templates must, therefore, be used for detecting defects of different sizes and shapes. In order for this detection process to be independent of defect size and shape, too numerous a number of templates would have to be compared to the two-dimensional image to detect all possible flaw sizes and shapes that may be present; such a process would be computationally impractical. Thus, the template matching technique can result in erroneous results if the template does not correspond substantially to the defect and the technique is inefficient because of the large catalog of templates which must be compared to the two-dimensional image.

SUMMARY OF THE INVENTION

It is, accordingly, a primary object of the present invention to provide a novel method for inspecting a gas turbine engine component having a complex geometric shape which is not subject to the foregoing disadvantages.

It is another object of the present invention to provide a novel method for inspecting gas turbine engine components which has a high probability of detecting flaws and is capable of distinguishing between geometric features of the component and actual defects or cracks in the component to minimize false indications.

It is a further object of the present invention to provide a novel method for inspecting a gas turbine engine component which can be automated and can be easily integrated into a production environment.

In accordance with the present invention, a method for inspecting a component of a gas turbine engine or the like having a plurality of similarly shaped structural portions, such as the gear teeth of a gear, the dovetail slots of a turbine disk or the like, includes the steps of: scanning a surface of at least one of the similarly shaped structural portions with an eddy current probe means to induce eddy currents in the component; generating a two-dimensional image of the at least one portion from eddy current signals received during scanning, each image including a multiplicity of pixels arranged in a two-dimensional array and each pixel having a gray scale intensity responsive to the eddy current induced in the component at a component location corresponding to a position of the pixel in the matrix array; preprocessing the image to substantially reduce or cancel out any signals or changes in the gray scale intensity of any pixels relative to the background pixel intensities in the image caused by geometrical characteristics and background noise common to all similarly shaped structural portions; identifying any suspected defect regions from the preprocessed image; determining a defect signal for each suspected defect region; and rejecting the component if any defect signal exceeds a predetermined reference value.

These and other objects of the present invention, together with the features and advantages thereof, will become apparent from the following specification when read with the accompanying drawings.

BRIEF DESCRIPTION OF THE DRAWINGS

FIG. 3 is an illustration of a portion of a two-dimensional digital image showing the individual picture elements or pixels.

FIG. 4 is an illustration of a 7×3 digital filter in accordance with the present invention.

FIG. 5 is an illustrated example of a binary image generated from a gray scale image by thresholding.

FIG. 6 is an illustration of a 9×2 digital filter in accordance with the present invention.

DETAILED DESCRIPTION OF THE PREFERRED EMBODIMENT

Figure 1:
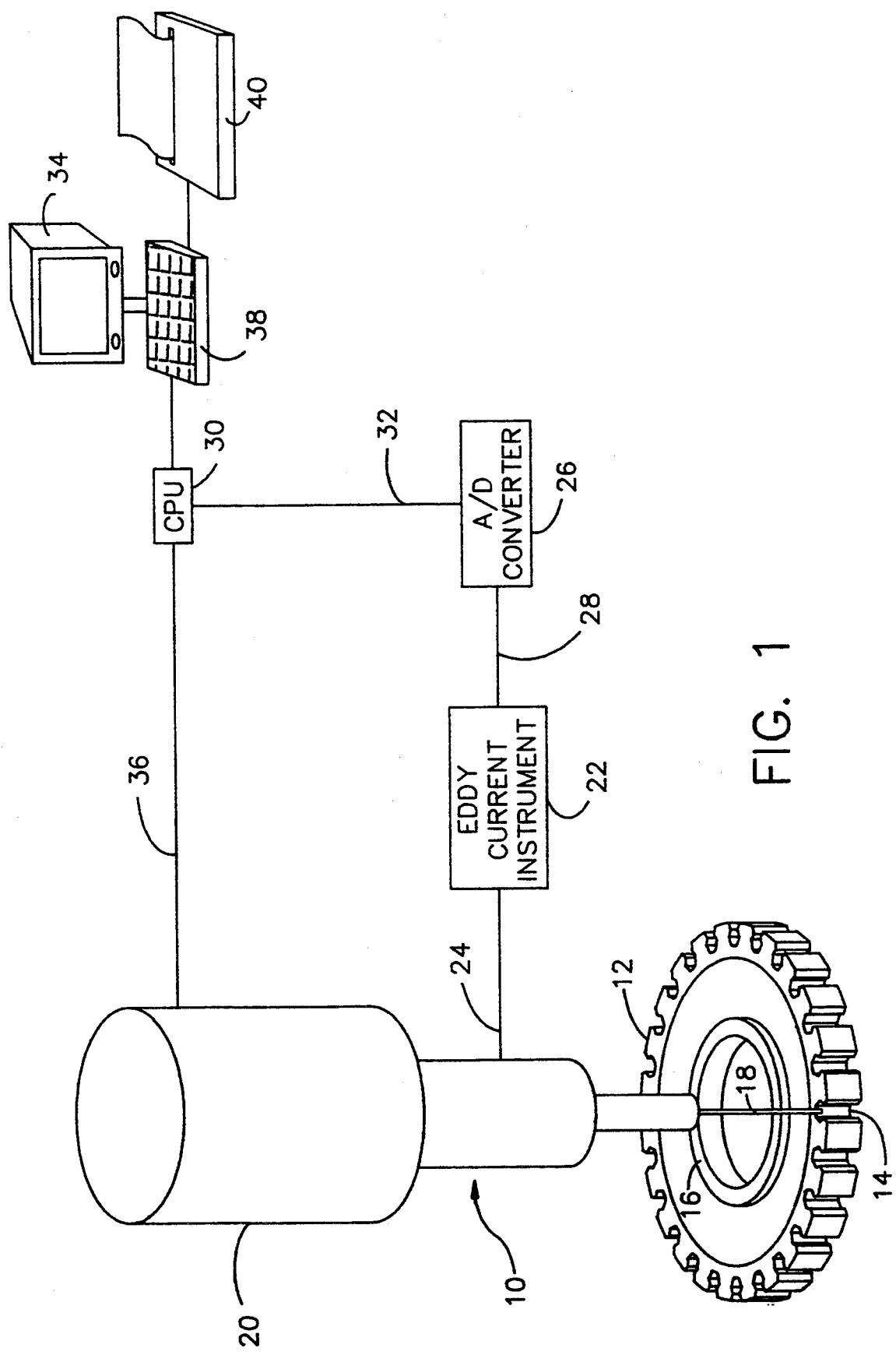
FIG. 1 is a schematic diagram of an automated eddy current surface flaw detection system in accordance with the present invention.

Referring initially to FIG. 1, an automated eddy current surface flaw detection apparatus 10 for inspecting a workpiece 12, such as the gear teeth of a gear, dovetail slots 14 of a gas turbine engine disk or the like, is illustrated. For purposes of convenience, the present invention will be described with respect to inspecting the dovetail slots 14 of a gas turbine engine disk 12; although, those skilled in the art will recognize that the present invention could equally be used to inspect any workpiece having a complex geometry which repeats or includes a plurality of similarly shaped portions, such as the gear teeth of a gear or the dovetail slots 14 of a turbine disk 12.

The turbine disk 12 is mounted on a fixture 16 of eddy current apparatus 10 to hold disk 12 in place during inspection. Apparatus 10 further includes a differential eddy current coil/probe 18, such as a GE ECII as manufactured by the General Electric Company, a PS-4 as manufactured by Nortech, Inc., or the like. Eddy current probe 18 may also be a probe array such as that disclosed in co-pending patent application Ser. No. 07/696,455 (RD-20,138), entitled "Eddy Current Probe Arrays", filed May 6, 1991, and assigned to the same assignee as the present application. Eddy current probe 18 is mounted to a probe manipulator 20 which moves probe 18 within dovetail slot 14 to substantially completely scan the interior of slot 14 during inspection. The manipulator 20 is preferably a 6-axis manipulator such as a Unidex as manufactured by Aerotech Inc., or the like. Eddy current probe 18 is electrically connected to an eddy current instrument 22 by a data link 24. Eddy current instrument 22 generates electrical signals responsive to the eddy currents induced within the surface of dovetail slot 14 during scanning of the slot by probe 18. The electrical signals generated by eddy current instrument 22 are received by an analog to digital (A/D) converter 26 over data communications link 28. A/D converter 26 may be a DVME 601E, as manufactured by Datel or the like which converts the analog eddy current signals to digital signals which can be stored and processed by a central processing unit (CPU) 30 to generate a two-dimensional digital image of dovetail slot 14. The digital signals are transmitted from A/D converter 26 to CPU 30 by a communications link 32. The two-dimensional digital images may be displayed on a video monitor 34. Computer 30 is also interconnected to probe manipulator 20 by a communications link 36 to control the scanning of the dovetail slots 14. A keyboard 38 is provided to facilitate operator control of the inspection of disk 12 and a printer 40 may be provided to generate hard copies of the images.

Figure 2A:
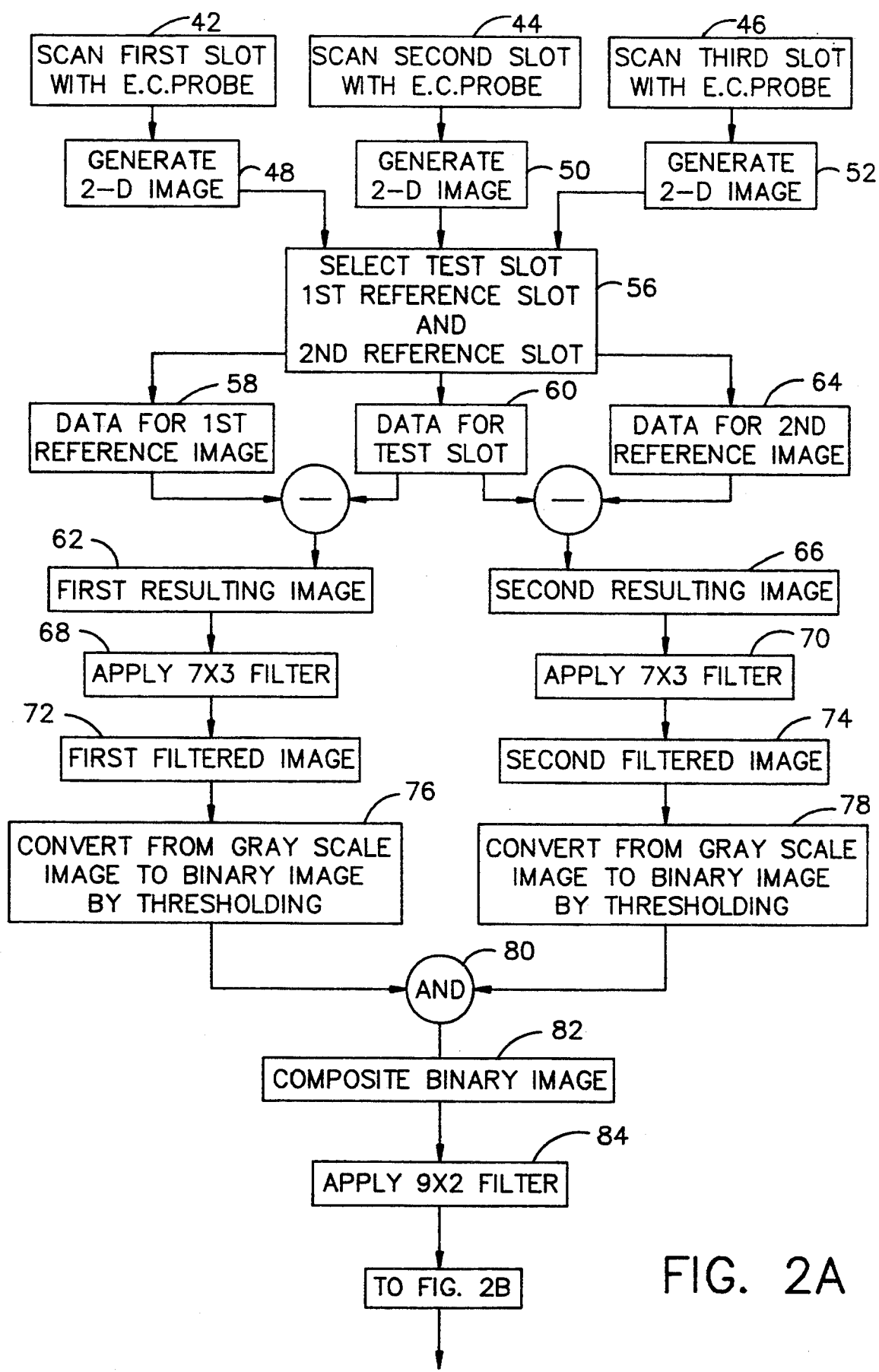
FIGS. 2A and 2B are a flow graph of the automated eddy current surface inspection method in accordance with the present invention.
Figure 2B:
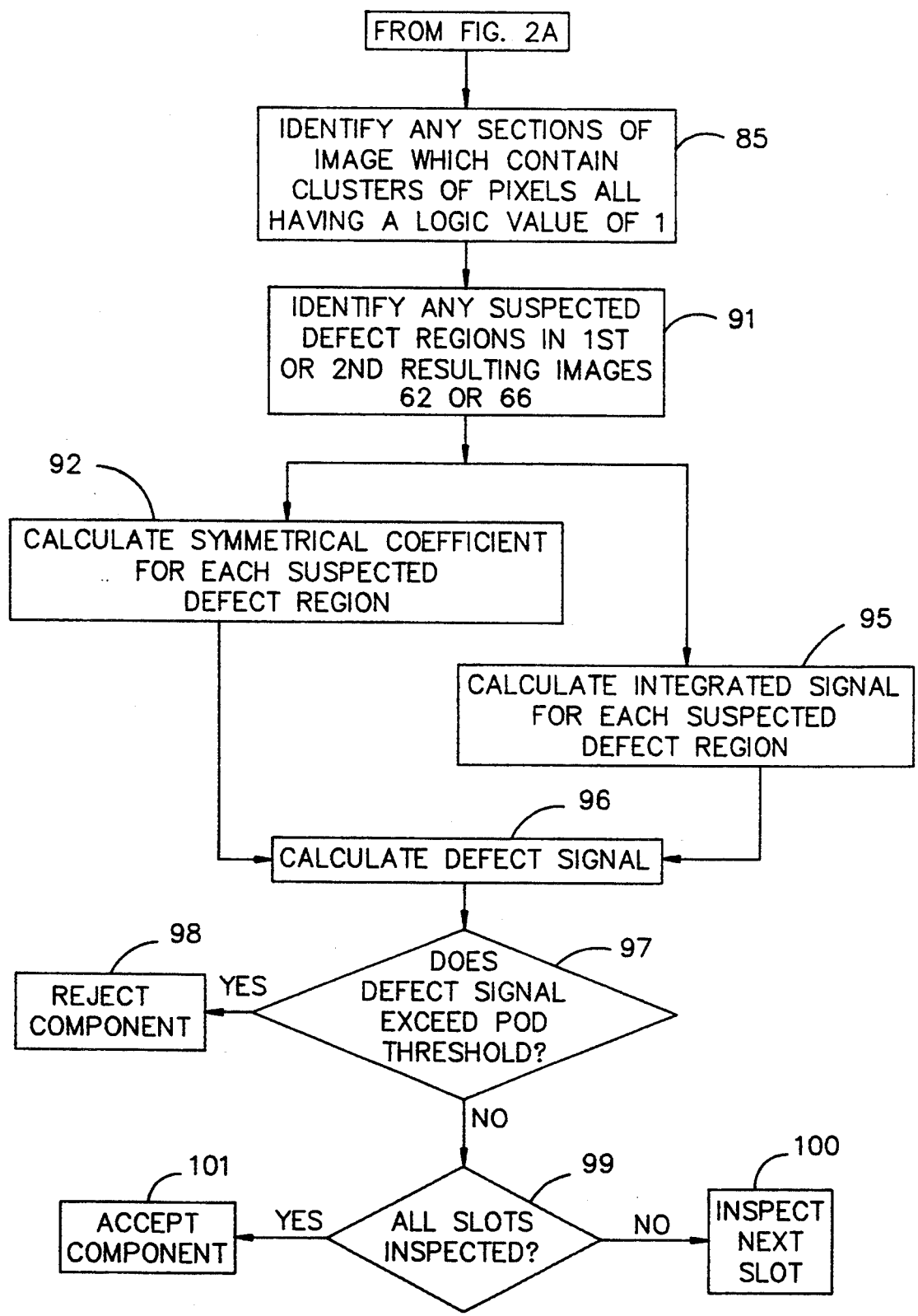

Referring now to FIGS. 2A and 2B, in accordance with the present invention, three dovetail slots 14 are each substantially completely scanned with the eddy current probe 18 of device 10 as indicated by blocks 42, 44 and 46 in FIG. 2A. As previously discussed, A/D converter 26 converts the analog eddy current signals from eddy current instrument 22 to digital signals which are stored by CPU 30 and combined after the scanning operation of each dovetail slot 14 to provide a two-dimensional digital image of each of the three dovetail slots 14, blocks 48, 50 and 52. Each of the two-dimensional images includes a multiplicity of picture elements or pixels 54 as illustrated in FIG. 3. The pixels 54 are usually arranged in uniform columns and rows to form an X-Y matrix type structure. Each of the pixels has a gray scale intensity ($I_{ij}$) which corresponds to the eddy current signal at the location on the dovetail slot surface represented by the particular pixel 54 or group of pixels; thus, changes in the gray scale intensity of the pixels 54 making up each of the three images results from local changes in each of the three dovetail slots 14 caused by the induced eddy currents. Changes in the component geometry such as edges, transitions between convex, concave and flat surfaces, other surface anomalies and flaws or defects will cause local changes in the eddy current signal which results in differences in the gray scale intensities ($I_{ij}$) of the pixels composing the two-dimensional digital images at those locations in the image corresponding to where the part geometry changes or where a defect or flaw is located.

Prior to scanning the three dovetail slots, the eddy current probe is preferably calibrated using a known test block which contains flaws or defects of substantially the same dimensions and shape as those expected to be encountered during inspection of the component 12. Calibrating the eddy current probe ensures that the eddy current voltage will remain within a selected range during component inspection so that the results will be uniform and reliable for the inspection of each dovetail slot 14 of component 12.

A test slot or slot under inspection, a first reference slot and a second reference slot are selected from the three dovetail slots 14 which were scanned as indicated in block 56 of FIG. 2A. The two-dimensional digital image of the slot under inspection, now referred to as the test slot image, block 60, is preprocessed to substantially reduce any signals or changes in the gray scale intensity of any pixels relative to the background pixel intensities in the image caused by geometrical characteristics, such as edges, transitions between convex, concave and flat regions or the like, or background noise common to all slots. Preprocessing the test slot image includes subtracting the two-dimensional digital image of the first reference slot, now referred to as the first reference image, block 58, from the two-dimensional test slot image 60, to provide a first resulting image at block 62, and also subtracting the two-dimensional image of the second reference slot, now referred to as the second reference image, block 64, from the test image 60 to provide a second resulting image at block 66. The images are subtracted by subtracting the gray scale intensities of the corresponding pixels in each image. For example, referring to FIGS. 2A and 3, $I_{11}$ of the first reference image 58 would be subtracted from $I_{11}$ of the test image 60, $I_{12}$ of the first reference image 58 would be subtracted from $I_{12}$ of the test slot image 60 and so forth for each of the pixels 54 in the first reference image 58 and test slot image 60 to provide the first resulting image 62. Similarly, $I_{11}$ of the second reference image 64 would be subtracted from $I_{11}$ of the test slot image 60, $I_{12}$ of the second reference image 64 would be subtracted from $I_{12}$ of the test slot image 60 and so forth for each of the pixels 54 of the second reference image 64 and test slot image 60 to provide the second resulting image 66. Subtracting the images causes geometric features which are common to all slots to substantially cancel out in the resulting images 62 and 66. A copy of at least one of the first or second resulting images 62 or 66 is stored for use in a subsequent step.

Each of the first and second resulting images 62 and 66 are then preferably filtered, blocks 68 and 70 in FIG. 2A, to reduce any noise signals present in the resulting images and to enhance any signals that may be caused by a defect. The filtering is preferably accomplished by image convolution using a 7×3 digital filter as shown in FIG. 4 to provide respective first and second filtered images, blocks 72 and 74 in FIG. 2A. The 7×3 digital filter matrix values of FIG. 4 were determined by applying the method of the present invention to test blocks having defects or flaws formed therein with known dimensions and shapes similar to those which would desirably be detected in the surface of a dovetail slot 14 of a gas turbine engine disk 12. The filter matrix values of FIG. 4 were selected to provide superior dovetail slot inspection results when detecting defects in the slots as small as about 4 mils with a probability of detection (POD) of about 95% and a confidence level of about 50%. The matrix values shown in FIG. 4 may be different depending, for example, upon the geometry of the component being inspected, the size of the defect desired to be detected and the desired POD and confidence level. Superior filter values can, therefore, be determined by inspecting test samples with known defects or cracks.

In another embodiment of the present invention, the filtering in blocks 68 and 70 may be accomplished by image convolution using a set of electrical signals corresponding to apriori defect feature information characteristic of the defects desired to be detected. A plurality of template means or filters may be provided with each template means embodying at least one predetermined apriori defect signal feature and each of the template means being predetermined to select at least one specific defect signal feature from each of the resulting images 62 and 66. Selected template means may be compared individually, by image convolution, to each of the resulting images 62 and 66 to comparatively extract respective apriori features from each resulting image. The desired defect features are comparatively extracted by calculating a respective correlation coefficient between the defect signal feature, characterized in the particular template means being compared, and the signals corresponding to each of the resulting images 62 and 66. Depending upon the value of the correlation coefficient a distinction can be made between those signals in the resulting images which may represent an actual defect and those signals which represent other surface anomalies, such as edges or transitions between convex, concave or flat surfaces. Preferably, a plurality of template means collectively cooperate as a composite template to detect a corresponding plurality of defect signal features in each resulting image 62 and 66.

Each of the first and second filtered images 72 and 74 is converted from a gray scale image to a respective first and second binary image 76 and 78 by thresholding. A selected gray scale threshold intensity value or level is determined by evaluating test blocks or test samples with known defect sizes to provide optimum detection of defects having a desired size or dimensions and to minimize false indications of defects caused by other anomalies in the surface of the dovetail slot 14. Therefore, the gray scale threshold level is determined as a function of the size of the defect desired to be detected and the desired POD and confidence level. The gray scale images are converted to binary images by assigning a logic 1 (or logic 0 depending upon whether it is desired that the suspected defects be represented in the binary image as a white area with a black background or as a black area with a white background) to those pixels 54 in the first and second filtered images 72 and 74 having a gray scale intensity greater than or equal to the selected threshold intensity value and by assigning a logic 0 (or logic 1) to those pixels 54 in each of the first and second filtered images 72 and 74 which have a gray scale intensity less than the selected threshold value. A sample configuration includes a threshold value of about 600 millivolts$^{\frac{1}{2}}$inches$^{\frac{1}{2}}$which may be used for detecting defects of about 4 mils in a dovetail slot of a gas turbine engine disk with a POD of about 95% and a confidence level of about 50%. The specific configuration is system dependent relying for example upon system gain.

The first and second binary images 76 and 78 are combined by performing a logic AND operation 80 to provide a composite binary image 82. An example of a composite binary image 82 is shown in FIG. 5. Because of the nature of the logic AND operation 80 in FIG. 2A, a gap or hole may be created in the composite binary image 82. A 9×2 digital filter 84 such as that shown in FIG. 6 may be applied to the composite binary image, as indicated in FIG. 2A, to fill in gaps or holes created during the AND operation 80.

If a logic 1 was selected during the thresholding operations 76 and 78 to identify those pixels 54 having a gray scale intensity greater than or equal to a selected threshold value to identify those regions or sections in the composite binary image 82 which may contain a defect or crack, then those regions or sections of the composite binary image 82 which contain a cluster or grouping of pixels 54 with predominately all pixels having a logic 1 value are identified as regions of interest which may contain a flaw or defect, block 85 in FIG. 2B. For example, referring to FIG. 5, three regions of interest, which may contain a defect, are each bounded by a chain line indicated by reference numerals 86, 88 and 90, respectively.

Figure 7:
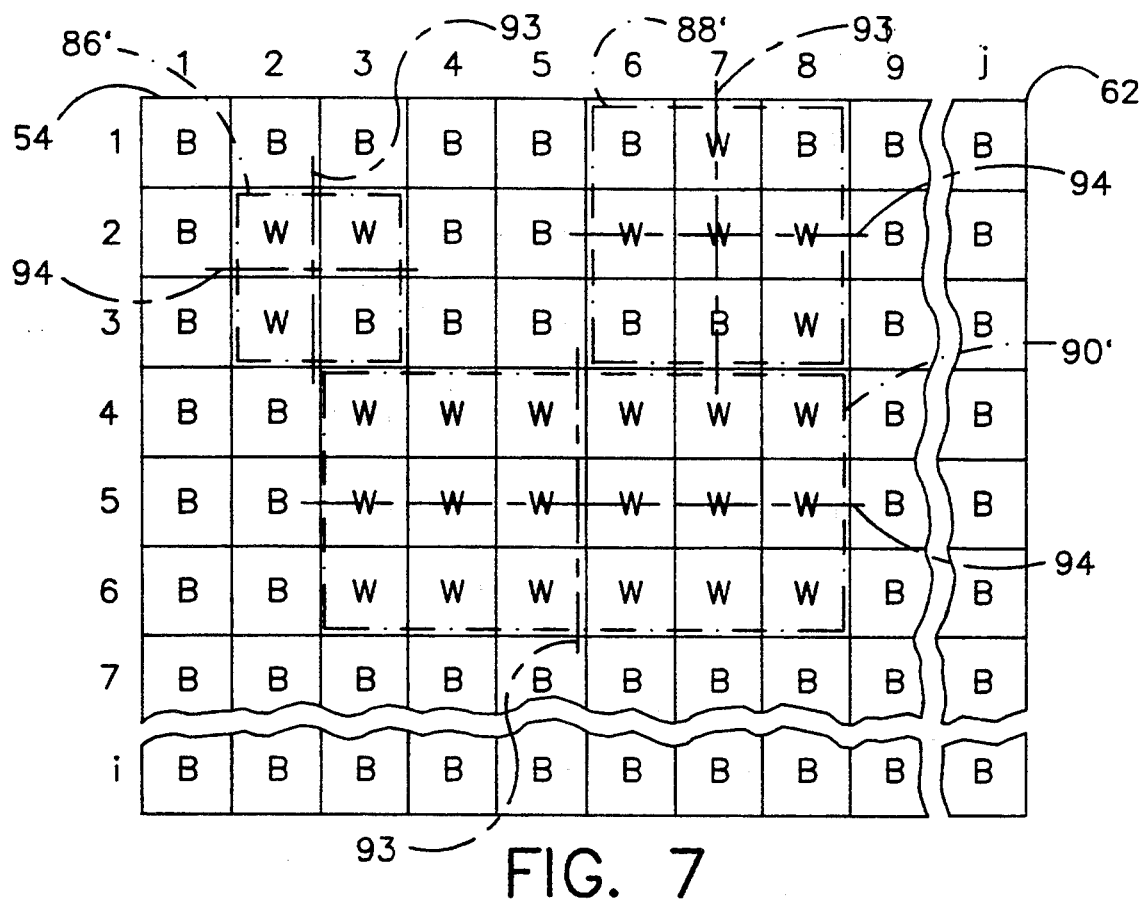
FIG. 7 is an illustrated example of a two-dimensional digital image which has been processed for calculating a Symmetrical Coefficient and an Integrated Signal for each suspected region which may contain a defect.

Regions of interest or suspected defect regions corresponding to the regions 86, 88 and 90 in the composite binary image are identified in either the first or second resulting images 62 or 66 of FIG. 2A as indicated in block 91 of FIG. 2B. FIG. 7 is an illustration of one of the two two-dimensional digital images 62 or 66 resulting from subtracting each of the first and second reference images 58 and 64 from the test image 60 as indicated in FIG. 2A. The regions of interest in the resulting image 62 (or 66) of FIG. 7, which correspond to the suspected defect regions 86, 88 and 90 of the composite binary image 82 in FIG. 5, are each bounded by a chain line and indicated by reference numerals 86', 88' and 90', respectively. The letter "B" within a pixel 54 in FIG. 7 represents a black pixel and the letter "W" within a pixel 54 represents a white pixel in the resulting image 62. The black and white pixels 54 indicated in FIG. 7 may actually be some intermediate gray scale intensity but will appear to be either predominantly black or predominantly white.

Referring also back to FIG. 2B, in accordance with the present invention, a symmetrical coefficient for each suspected defect region is calculated from the pixel intensities within each region 86', 88' and 90', block 92. To calculate the symmetrical coefficient, each suspected defect region 86', 88' and 90' is vertically and horizontally bisected as represented by respective broken lines 93 and 94 in each of regions 86', 88' and 90' of FIG. 7. The symmetrical coefficient is a measure of the symmetry of the gray scale pixel intensities on opposite sides of each of the vertical bisecting lines 93 and horizontal bisecting lines 94 for each of the regions of interest 86', 88' and 90'. The symmetrical coefficient is determined by calculating a first percentage of corresponding pixels 54 on opposite sides of vertically bisecting line 93 which have substantially the same gray scale intensity and by calculating a second percentage of corresponding pixels 54 on opposite sides of horizontally bisecting line 94 which have substantially the same gray scale intensity for each region of interest 86', 88' and 90'; the first and second percentages for each region are then multiplied to provide a symmetrical coefficient for each respective region 86', 88' and 90'. The coefficient of symmetry can range from a +1 which represents an ideal symmetrical region to a −1 which represents a non-symmetrical region. Region 90' in FIG. 7 is an example of an ideal symmetrical region while regions 86' and 88' represent some percentage of complete symmetry between the range from +1 to −1.

For each region of interest 86', 88' and 90' in the resulting image 62, an integrated signal is also calculated, block 95 in FIG. 2B, from the gray scale intensity values of each pixel 54 within each of the regions of interest. The integrated signal 95 is the sum of all gray scale pixel values within the boundary of each of the regions of interest 86', 88' and 90'.

In accordance with the present invention, a defect signal is calculated, block 96 in FIG. 2B, from the symmetrical coefficient 92 and the integrated signal 95 for each region of interest 86', 88' and 90'. The defect signal 96 is referred to as AHAT (a) and is calculated in accordance with the following equation:

$$AHAT + (\text{Symmetrical Coef.})^\alpha \times (\text{Integrated Signal})^\gamma \times (\text{Area of Region})^\beta$$

where $\alpha$, $\gamma$ and $\beta$ are determined by applying the method of the present invention to test parts or samples having defects of known dimensions and shapes formed therein to provide sufficient detection sensitivity, at a desired POD and confidence level, with the minimum number of false calls or indications that a defect is present when not. Values of $\alpha=1$, $\beta=\frac{1}{4}$ and $\gamma=\frac{1}{4}$ were determined empirically to provide superior detection results when detecting defects in dovetail slots as small as about 4 mils with a POD of about 95% and a confidence level of about 50%. The defect signal 96 or AHAT is compared against a reference value or POD threshold, block 97 in FIG. 2B, and the component is rejected if AHAT exceeds this reference value, block 98. If the POD threshold is not exceeded then a determination is made as to whether all slots 14 have been inspected, block 99. If additional slots 14 need to be tested, the process described hereinabove is repeated to inspect the next slot, block 100, until all dovetail slots 14 of disk 12 have been designated as the test slot 60 and have been inspected. A slot 14 which has already been scanned but was previously selected as a reference slot, blocks 58 and 64 of FIG. 2A, would not necessarily have to be scanned again in the interest of efficiency. If all slots 14 are inspected without AHAT exceeding the POD threshold then the component 12 is accepted, block 101.

Figure 8:
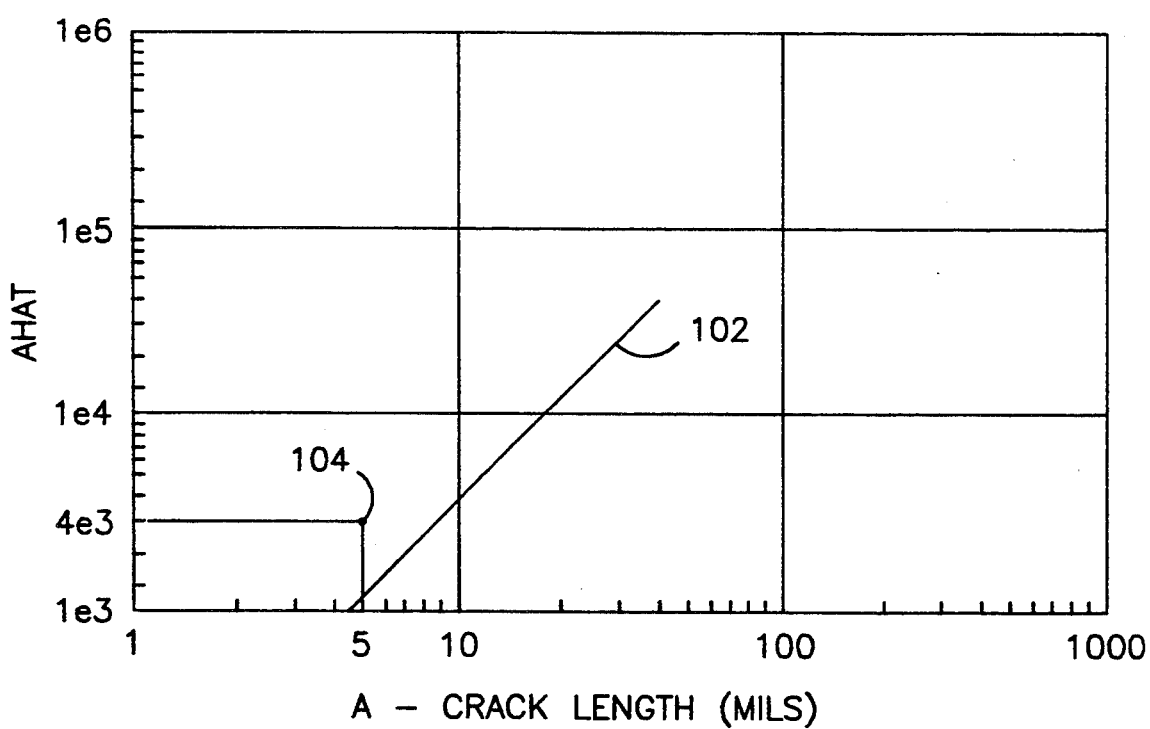
FIG. 8 is a probability of detection (POD) plot for a dovetail slot of a gas turbine engine disk made from Rene 88 material.

Values for AHAT have been computed for various known defect or crack lengths in mils, predetermined probabilities of detection (POD) and confidence levels for different materials. The AHAT values have been plotted against the crack lengths to provide standard POD curves or graphs for different materials for use in the industry. As an example, a POD curve 102 for inspecting dovetail slots made of Rene 88 is shown in FIG. 8. Thus, the defect signal or A}{AT calculated in block 96 can be plotted on a POD curve, similar to graph 102, for the particular material and component under inspection according to the estimated length of the crack as determined from the length of the suspected defect region as measured from the resulting image 62 shown in FIG. 7. Therefore, if the AHAT value is on or above the curve 102 shown in FIG. 8 then the component 12 is rejected; if AHAT is below the curve 102 then the next slot 14 is inspected until all the slots 14 have been tested. If all slots 14 pass, then the component 12 is accepted. For example, assume that AHAT for region 90' in FIG. 7 is calculated to be about 4,000 using the equation indicated hereinabove; additionally, assume that the crack length within the region of interest 90' is estimated from the resulting image 62 to be about 5 mils. This corresponds to point 104 in FIG. 8 which is greater than the POD curve 102; therefore, the component would be rejected.

While the present invention was described with respect to inspecting dovetail slots formed in a disk of a gas turbine engine, those skilled in the art will readily recognize that the present invention is not limited to inspecting dovetail slots but that the invention can be applied to inspect any conductive workpiece with a complex geometric shape. Applying the method of the present invention, after scanning the workpiece under inspection with an eddy current probe to generate an image responsive to the eddy currents induced in the workpiece, the difference between a reference image of a workpiece having substantially the same geometric shape and the generated image of the workpiece under inspection is taken to provide a resulting image in which signals caused by geometrical characteristics and background noise, common to all of the similarly shaped workpieces, are substantially reduced or cancelled out. In accordance with the method of the present invention, the resulting image may be converted to a binary image to facilitate identification of any suspected defect regions and a defect signal may be determined for each suspected defect region from a stored version of the resulting image. The workpiece is rejected if the defect signal exceeds a predetermined reference value.

Different embodiments and adaptations of the present invention besides those shown herein and described, as well as many variations, modifications and equivalent arrangements will now be apparent and will be reasonably suggested by the foregoing specification and drawings, without departing from the substance or scope of the invention. While the present invention is described herein in detail in relation to its preferred embodiments, it is to be understood that this disclosure is only illustrative and exemplary of the present invention and is made merely for purposes of providing a full and enabling disclosure of the invention. Accordingly, it is intended that the invention is limited only by the spirit and scope of the claims appended hereto.

What is claimed is:

1. A method for inspecting a component having a plurality of similarly shaped structural portions, comprising the steps of:

(a) scanning a surface of at least one of the similarly shaped structural portions with an eddy current probe means to induce eddy currents in the component;

(b) generating a two-dimensional image of the at least one portion from eddy current signals received during scanning, the image including a multiplicity of pixels arranged in a two-dimensional matrix array and each pixel having a gray scale intensity responsive to the eddy current induced in the component at a component location corresponding to a position of the pixel in the two-dimensional matrix array;

(c) preprocessing the image to substantially reduce any signals caused by geometrical characteristics and background noise common to all of the similarly shaped structural portions;

(d) identifying any suspected defect regions in the two-dimensional image from corresponding regions in the preprocessed image of step (c);

(e) determining a defect signal from the gray scale intensities for each suspected defect regions in the two-dimensional image; and (f) rejecting the component if any defect signal exceeds a predetermined reference value, wherein step (c) comprises the steps of:

(c1) repeating steps (a) and (b) to generate a two-dimensional image for a second and third similarly shaped structural portion;

(c2) selecting a test portion and an associated test image, a first reference portion and an associated first reference image, and a second reference portion and an associated second reference image from the three similarly shaped portions;

(c3) taking a difference between the first reference image and the test image to provide a first resulting image by taking a difference between the gray scale intensity of each pixel of the first reference image and the gray scale intensity of a corresponding pixel of the test image;

(c4) taking a difference between the second reference image and the test image to provide a second resulting image by taking a difference between gray scale intensities of corresponding pixels of each image;

(c5) converting each of the first and second reference images from a gray scale image to respective first and second binary images; and (c6) combining the first and second binary images by a logic AND operation to provide a preprocessed composite binary image.

2. The method of claim 1, wherein step (d) comprises the steps of:

identifying any sections within the preprocessed composite binary image which contain a cluster of pixels with predominantly all pixels having a predetermined binary value; and identifying any suspected defect regions in one of the first and second resulting images which correspond to the identified sections in the preprocessed composite binary image.

3. The method of claim 1, wherein steps (c5) and (c6) are replaced by:

(c5') combining the first and second resulting images to provide a composite image; and (c6') converting the composite image to a preprocessed composite binary image.

4. The method of claim 3, wherein step (d) comprises the steps of:

identifying any sections within the preprocessed composite binary image which contain a cluster of pixels with predominantly all pixels having a predetermined binary value; and identifying any suspected defect regions in one of the first and second resulting images which correspond to the identified sections in the preprocessed composite binary image.

5. The method of claim 1, further comprising the step of filtering each of the first and second resulting images to reduce any signals caused by noise in each image and to enhance any signals caused by a defect before step (c5).

6. The method of claim 5, wherein the filtering is accomplished by image convolution using a digital filter.

7. The method of claim 5, wherein the filtering step comprises the step of applying a set of predetermined apriori signals to each of the first and second resulting images by image convolution to extract selected features of any defect signal from each of the resulting images.

8. The method of claim 7, wherein the step of applying a set of predetermined apriori signals comprises the step of providing a template means for comparing at least one predetermined apriori signal of a selected feature to each resulting image.

9. The method of claim 8, wherein image convolution comprises the step of providing at least one template means for comparatively extracting respective apriori features from each resulting image.

10. The method of claim 9, wherein a plurality of template means are compared to each of the resulting images, each of the template means being predetermined to select at least one specific defect signal feature from each resulting image.

11. The method of claim 10, wherein the plurality of template means collectively cooperate as a composite template to detect a corresponding plurality of defect signal features in each resulting image.

12. The method of claim 9, wherein the step of comparatively extracting comprises the step of calculating a respective correlation coefficient between each signal feature characterized in the template means and signals corresponding to each of the resulting images.

13. The method of claim 1, further comprising the step of repeating steps (a)–(f) until all similarly shaped structural portions have been inspected.

14. A method for inspecting a component having a complex geometric shape, comprising the steps of:

(a) scanning a surface of the component with an eddy current probe means to induce eddy currents in the component;

(b) generating a two-dimensional image of the component from eddy current signals received during scanning, the image including a multiplicity of pixels arranged in a two-dimensional matrix array and each pixel having a gray scale intensity responsive to the eddy current induced in the component at a component location corresponding to a position of the pixel in the two-dimensional matrix array;

(c) preprocessing the image to substantially reduce any signals caused by geometrical characteristics and background noise common to all components having substantially the same geometric shape by subtracting a reference image of a substantially identically shaped component from the image generated in step (b);

(d) identifying any suspected defect regions in the two-dimensional image from corresponding regions in the preprocessed image of step (c); and (e) determining a defect signal from the gray scale intensities for each suspected defect region in the two-dimensional image;

(f) rejecting the component if any defect signal exceeds a predetermined reference value, converting the preprocessed image from a gray scale image to a binary image;

identifying any sections within the binary image which contain a cluster of pixels with predominantly all pixels having a predetermined binary value; and identifying any suspected defect regions in the preprocessed image which correspond to the identified sections in the preprocessed composite binary image.

15. The method of claim 14, further comprising the step of filtering the preprocessed image before converting to a binary image, to reduce any signals caused by noise and to enhance any signals caused by a defect.

16. A method for inspecting dovetail slots of a gas turbine engine component, comprising the steps of:

(a) scanning a surface of a dovetail slot with an eddy current probe means to induce eddy currents in the component;

(b) generating a two-dimensional image of the dovetail slot surface from eddy current signals received during scanning, each image including a multiplicity of pixels arranged in a two-dimensional matrix array and each pixel having a gray scale intensity responsive to the eddy current induced in the component at a component location corresponding to a position of the pixel in the two-dimensional matrix array;

(c) repeating steps (a) and (b) to generate a two-dimensional image for three dovetail slots;

(d) selecting a test slot and an associated test image, a first reference slot and an associated first reference image, and a second reference slot and an associated second reference image from the three dovetail slots;

(e) taking a difference between the first reference image and the test image to provide a first resulting image by taking a difference between the gray scale intensity of each pixel of the first reference image and the gray scale intensity of a corresponding pixel of the test image;

(f) taking a difference between the second reference image and the test image to provide a second resulting image by taking a difference between gray scale intensities of corresponding pixels of each image;

(g) converting each of the first and second resulting images from a gray scale image to respective first and second binary images by thresholding;

(h) combining the first and second binary images by a logic AND operation to provide a composite binary image;

(i) identifying any sections within the composite binary image which contain a cluster of pixels with predominantly all pixels having a predetermined binary value;

(j) identifying any suspected defect regions in one of the first and second resulting images of step (e) which correspond to the identified sections of step (i);

(k) calculating a defect signal for each suspected defect region; and (l) comparing the defect signal for each region with a predetermined reference value to determine whether a defect is present in the test slot at a location corresponding to the suspected defect region.

17. The method of claim 16, further comprising the step of filtering each of the first and second resulting images before step (g), to reduce signals caused by noise in each image and to enhance any signals which may be caused by a defect, by image convolution using a digital filter.

18. The method of claim 17, wherein the step of filtering includes convoluting each of the first and second resulting images with a $7 \times 3$ digital filter.

19. The method of claim 18, wherein the $7 \times 3$ digital filter has the following matrix array:

$$\begin{array}{ccccccc} 0 & 0 & 0 & 1 & 0 & 0 & 0 \\ -1 & 0 & 0 & 0 & 0 & 0 & 1 \\ 0 & 0 & 0 & -1 & 0 & 0 & 0. \end{array}$$

20. The method of claim 16, further comprising the step of applying a digital filter to the composite binary image after step (h) by image convolution.

21. The method of claim 20, wherein the digital filter is a $9 \times 2$ filter having the following matrix array:

$$\begin{array}{ccccccc} 1 & 1 & 1 & 1 & 1 & 1 & 1 \\ 1 & 1 & 1 & 1 & 1 & 1 & 1. \end{array}$$

22. The method of claim 16, wherein step (k) comprises the steps of:

(k1) calculating a symmetrical coefficient for each suspected defect region of step (j) from the gray scale intensities within each respective region; and (k2) calculating an integrated signal for each suspected defect region of step (j) from the gray scale intensities within each respective region.

23. The method of claim 22, wherein step (k1) comprises the steps of:

bisecting each suspected defect region along a first selected dimension of each region;

calculating a first percentage of corresponding pixels in each half of each region which have substantially the same gray scale intensity;

bisecting each suspected defect region along a second selected dimension of each region;

calculating a second percentage of corresponding pixels in each half of each region bisected by the second selected dimension which have substantially the same gray scale intensity; and multiplying the first and second percentages of each region to provide a symmetrical coefficient for each region.

24. The method of claim 22, wherein the defect signal for each region is equal to AHAT and AHAT is determined according to the following equation:

$$AHAT = (\text{symmetrical coefficient})^\alpha \times (\text{area of the suspected defect region})^\beta \times (\text{integrated signal})^\gamma.$$

25. The method of claim 24, wherein $\alpha=1$, $\beta=\frac{1}{4}$, and $\gamma=\frac{1}{4}$.

26. The method of claim 16, further comprising the step of repeating steps (a)–(l) until all dovetail slots have been inspected.

27. The method of claim 16, further comprising the steps of:
- estimating a possible defect length for each suspected defect region;
- plotting a point on a probability of detection POD plot which corresponds to the defect signal versus the defect length for each suspected defect region; and
- rejecting the component if the plotted point for any suspected defect region exceeds a threshold curve of the POD plot.

28. A method for inspecting gear teeth and the like of a component, comprising the steps of:
- (a) scanning a surface of a gear tooth with an eddy current probe means to induce eddy currents in the component;
- (b) generating a two-dimensional image of the gear tooth surface from eddy current signals received during scanning, each image including a multiplicity of pixels arranged in a two-dimensional matrix array and each pixel having a gray scale intensity responsive to the eddy current induced in the component at a component location corresponding to a position of the pixel in the matrix array;
- (c) repeating steps (a) and (b) to generate a two-dimensional image for three gear teeth;
- (d) selecting a test tooth and an associated test image, a first reference tooth and an associated first reference image, and a second reference tooth and an associated second reference image from the three gear teeth;
- (e) taking a difference between the first reference image and the test image to provide a first resulting image by taking a difference between the gray scale intensity of each pixel of the first reference image and the gray scale intensity of a corresponding pixel of the test image;
- (f) taking a difference between the second reference image and the test image to provide a second resulting image by taking a difference between the gray scale intensities of corresponding pixels of each image;
- (g) converting each of the first and second resulting images from a gray scale image to respective first and second binary images by thresholding;
- (h) combining the first and second binary image by a logic AND operation to provide a composite binary image;
- (i) identifying any sections within the composite binary image which contain a cluster of pixels with predominantly all pixels having a predetermined binary value;
- (j) identifying any suspected defect regions in one of the first and second resulting images of step (e) which correspond to the identified sections of step (i);
- (k) calculating a defect signal for each suspected defect region; and
- (l) comparing the defect signal for each region with a predetermined reference value to determine whether a defect is present in the test tooth at a location corresponding to the suspected defect region.

29. The method of claim 28, further comprising the step of filtering each of the first and second resulting images before step (g), to reduce signals caused by noise in each image and to enhance any signals which may be caused by a defect, by image convolution using a digital filter.

30. The method of claim 28, further comprising the step of applying a digital filter to the composite binary image after step (h) by image convolution.

31. The method of claim 28, wherein step (k) comprises the steps of:
- (k1) calculating a symmetrical coefficient for each suspected defect region of step (j) from the gray scale intensities within each respective region; and
- (k2) calculating an integrated signal for each suspected defect region of step (j) from the gray scale intensities within each respective region.

32. The method of claim 31, wherein step (k1) comprises the steps of:
- bisecting each suspected defect region along a first selected dimension;
- calculating a first percentage of corresponding pixels in each half of each region which have substantially the same gray scale intensity;
- bisecting each suspected defect region along a second selected dimension;
- calculating a second percentage of corresponding pixels in each half of each region bisected by the second selected dimension which have substantially the same gray scale intensity; and
- multiplying the first and second percentages of each region to provide a symmetrical coefficient for each region.

33. The method of claim 31, wherein step (k2) comprises the step of summing the gray scale intensities of all pixels within each individual suspected defect region to provide an integrated signal for each region.

34. The method of claim 31, wherein the defect signal for each region is equal to AHAT and AHAT is determined according to the following equation:

$$AHAT = (\text{symmetrical coefficient})^\alpha \times (\text{area of the suspected defect region})^\beta \times (\text{integrated signal})^\gamma.$$

* * * * *